United States Patent [19]
Chirnside

[11] Patent Number: 5,773,235
[45] Date of Patent: Jun. 30, 1998

[54] EQUINE ARTERITIS VIRUS PEPTIDES; ANTIBODIES AND THEIR USE IN A DIAGNOSTIC TEST

[75] Inventor: Ewan D. Chirnside, Newmarket, United Kingdom

[73] Assignee: The Minister of Agriculture Fisheries & Food in her Britannic Majesty's Government of the United Kingdom of Great Britain and Northern Ireland, United Kingdom

[21] Appl. No.: 676,169
[22] PCT Filed: Jan. 13, 1995
[86] PCT No.: PCT/GB95/00066
§ 371 Date: Jul. 31, 1996
§ 102(e) Date: Jul. 31, 1996
[87] PCT Pub. No.: WO95/19438
PCT Pub. Date: Jul. 20, 1995

[30] Foreign Application Priority Data

Jan. 14, 1994 [GB] United Kingdom ............ 9400656

[51] Int. Cl.[6] ............ A61K 39/12; G01N 33/53; C12P 21/02; C07K 16/08
[52] U.S. Cl. ............ 435/7.92; 435/7.1; 435/69.1; 436/536; 530/388.3; 530/389.4; 536/23.72; 424/186.1
[58] Field of Search ............ 536/23.72; 530/388.3, 530/389.4; 424/186.1; 435/7.92, 7.1, 69.1; 436/536

[56] References Cited

PUBLICATIONS

Balasuriya et al. J Gen Virol vol. 74, 1993, pp. 2525–2529.
Boon et al. J Virol, vol. 65, No. 6, Jun. 1991, pp. 2910–2920.

*Primary Examiner*—Ponnathapura Achutamurthy
*Assistant Examiner*—Phuong T. Bui
*Attorney, Agent, or Firm*—Nixon & Vanderhye

[57] ABSTRACT

This invention provides a peptide or peptide conjugate of the equine arteritis virus $G_L$ protein which elicits an immune response in animals to whom the peptide or peptide conjugate is administered and results in the production of neutralizing antibodies against equine arteritis virus, the peptide or peptide conjugate corresponds to amino acid sequences of SEQ ID NOs:3, 4, 5, 6 and 7.

11 Claims, 2 Drawing Sheets

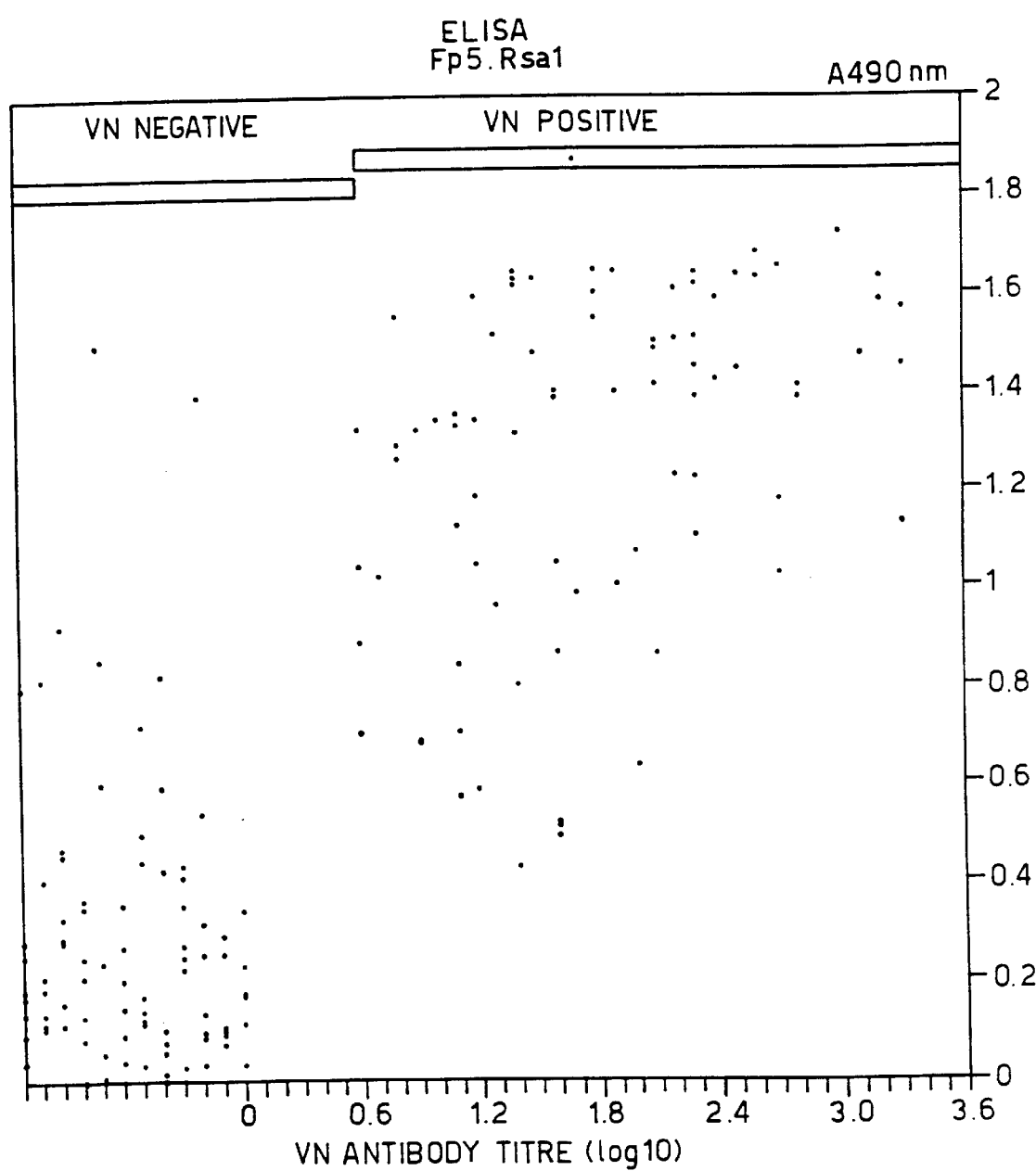

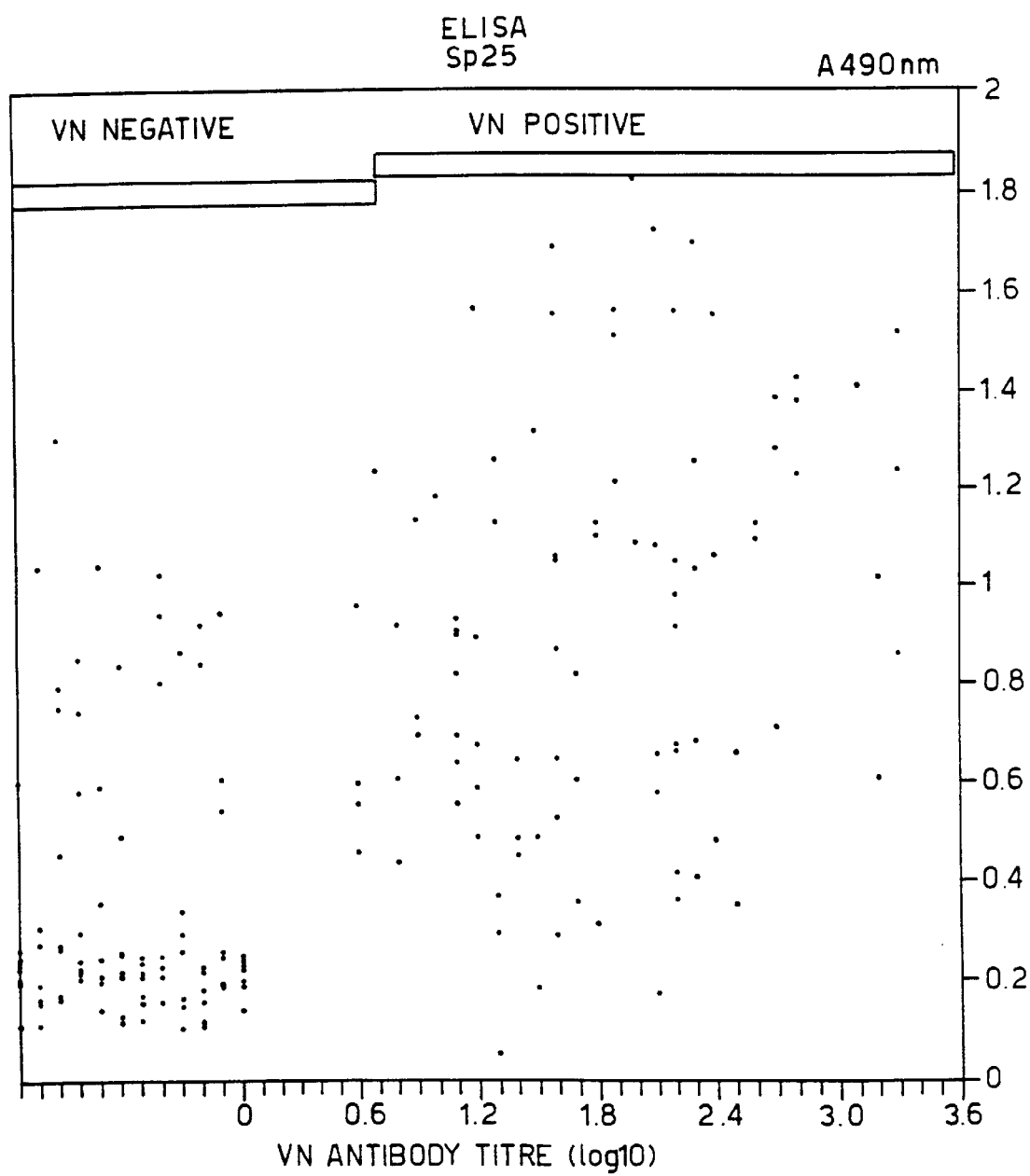

EQUINE ARTERITIS VIRUS PEPTIDES; ANTIBODIES AND THEIR USE IN A DIAGNOSTIC TEST

The present invention relates to recombinant DNA and proteins encoded thereby having use in provision of vaccines, diagnostics test kits and methods of diagnosis for equine arteritis virus (EAV) and equine arteritis virus mediated disease.

Equine viral arteritis, a disease for which horses and donkeys are the only reported hosts, has been known for some 40 years and manifests itself with widely varying clinical signs. In its most severe form EAV infection causes abortion which makes it a potentially significant commercial threat to, inter alia, the race horse breeding industry. Early veterinary articles refer to it as epizootic cellulitus pinkeye or equine influenza. Disease outbreaks are identified infrequently and field isolates of the single stranded RNA virus itself are rare.

The virus is transmitted by the respiratory and venereal routes, with a 30% carrier state existing in seropositive stallions making the latter route a particular cause for concern as these shedding stallions may consequently infect brood-mares. In the light of the potential economic importance of the virus and its stud carrier mediated infection capability there exist a requirement for both prophylactic treatment and reliable diagnosis of EAV.

Laboratory tests based upon ELISA, virus neutralisation (VN) and complement fixation (CF) formats have been developed (see Chirnside (1992) Br. vet. J. 148 pp118). The known ELISA is relatively insensitive when applied to tissues, eg. sera, from horses previously vaccinated for other diseases such as influenza and herpesvirus, while the VN and CF formats have limited temporal sensitivity; the VN test is unable to distinguish between vaccination and natural infection.

Vaccination procedures have concentrated on safety and efficacy of whole inactivated virus and attenuated live virus vaccine. The live vaccine can induce shedding of virus from the nasopharynx and does not prevent this causing infection of commonly housed animals that have not been so treated. The known formalinised vaccine does not provide reliable protection.

Attempts to provide improvements to both diagnostic tests and vaccines have included studies into panels of antibodies raised against various EAV proteins. A 29K envelope protein in particular has been identified as antigenic and capable of causing production of neutralising antibodies in mouse (Balasuriya et al (1993) Journal of General Virology, 74, p2525–2529). The identity of this protein is unknown but work reported since the priority date of the present application by Deregt et al (J. General Virology 75, pp2439–2444) has shown that some monoclonal antibodies raised to $G_L$ protein are EAV neutralising, as are those to the nucleocapsid N protein. Results of tests in horse have yet to be reported.

The present inventor now provides isolated peptides that produce a potent neutralising immune response against EAV when administered to animals, particularly horses, and these peptides provide sensitive detection of EAV antibodies when used as binding agent in binding assay format. Further provided is DNA encoding for these peptides.

In a first aspect of the present invention there is provided a peptide or peptide conjugate comprising one or more epitopes capable of evoking an immune response in animals producing antibodies which are neutralising to equine arteritis virus, characterised in that the epitopes are selected from those present in the amino acid sequence corresponding to amino acid 19 to 137 (SEQ ID No 3) of equine arteritis virus (EAV) $G_L$ protein; the peptide not being the $G_L$ protein.

Preferred peptides or peptide conjugates of the invention comprise the epitopes present in the amino acid sequence corresponding to amino acid 28 to 137 (SEQ ID No 4), more preferably 75 to 97 (SEQ ID No 5) and most preferably 85 to 97 (SEQ ID No 7) of EAV $G_L$. Preferred peptides or peptide conjugates comprise the amino acid sequence corresponding to amino acid 75 to 97 or a sequence having at least 90% homology thereto; preferably comprising an amino acid sequence corresponding to a sequence at least 90% homologous to the sequence of amino acids 28 to 137 of equine arteritis virus $G_L$ protein (SEQ ID No 4), but including said 85 to 97, or more preferably the 75 to 97 sequence, or a sequence that has at least 90% homology thereto. Other desirable optional epitopes identified are at 33 to 44 and 53 to 64.

A second aspect of the present invention provides a peptide or peptide conjugate comprising one or more epitopes capable of evoking an immune response in animals that produces antibodies which are neutralising to equine arteritis virus, characterised in that the epitopes are selected from those present in the amino acid sequence corresponding to amino acid 19 to 137 of equine arteritis virus $G_L$ protein (SEQ ID No 3), for use as a diagnostic agent; such peptide or conjugate is particularly provided for use as a diagnostic agent for the detection of EAV. Such aspect of course includes equine arteritis virus $G_L$ protein as such for these uses. Peptides or conjugates comprising SEQ ID No 2 are preferred; $G_L$ protein being included for such use; but peptides or conjugates comprising an amino acid sequence corresponding to a sequence at least 90% homologous to the sequence of amino acids 19 to 137 of equine arteritis $G_L$ protein (SEQ ID No 3) or to SEQ ID No 4, while retaining the amino acids 75 to 97 (SEQ ID No 5 and most preferably retaining the amino acids 85 to 97 (SEQ ID No 7) of, or having at least 90% homology to, SEQ ID No 2 may be used.

In a third aspect of the present invention are provided compositions comprising isolated peptides or peptide conjugates as described above per se, including $G_L$, particularly for use in evoking neutralising antibody responses, eg. for the purpose of prophylaxis or diagnosis. Typically such compositions will comprise a peptide or conjugate of the present invention together with a pharmaceutically acceptable carrier or a carrier suitable for use in binding studies respectively.

In a fourth aspect of the present invention there is provided recombinant DNA, or RNA derived therefrom, encoding for peptides or conjugates of the invention, and plasmids and cells transformed thereby comprising this DNA such that they are capable of expressing the peptides or conjugates. This DNA has sequences of SEQ ID Nos 3 to 7 and those indicated in Table 1 below, and may be incorporated into cells in the form of vectors such as plasmids or may be used as a 'naked vaccine' by way of chromosomal integration; both techniques being well understood by those skilled in the art.

In a fifth aspect of the present invention there is provided a method for testing for the presence of antibodies to equine arteritis virus comprising use of a peptide or peptide conjugate of the present invention, or $G_L$ protein, as a specific binding agent. Such test is preferably of ELISA format but may use the peptide or conjugate as immobilised binding agent or labelled secondary binding agent in a so called sandwich assay.

In binding assay where the peptide or peptide conjugate is immobilised this method may conveniently be carried out by use of commercially available assay plates onto which the peptide or conjugate is coated by suitable incubation in the known manner. For the purpose of assay a sample to be screened for EAV antibodies, eg. a serum sample, is typically incubated in contact with the plate, eg. in the wells, whereafter any EAV antibody present therein is identified by exposure to eg. an anti-horse IgA, IgG or IgM conjugated to a reporter group. Such reporter group may be in the form of a radiolabel, chemical label or a biological label. A typical biological label is an enzyme or cofactor, eg. biotin, and is detected by exposure to all the reactants necessary for a reporter reaction to occur dependent upon the presence of the reporter group. In the case of biotin the well may be exposed to streptavidin-peroxidase and then o-phenylenediamine dihydrochloride and the absorbance of the plate determined at 490 nm.

In a further example an immobilised anti-hors e IgA, IgM or IgG antibody raised in another animal may be used to bind a specific class of horse antibody and then the immobilised horse antibody provided may be exposed to a solution containing labelled peptide or conjugate of the invention whereby presence of anti-EAV antibody is indicated by assay of the amount of label present. Other assay formats such as competitive assays using either bound and unbound peptide or conjugate will occur to those skilled in the art; these will include simple observation of agglutination between peptide or conjugate and the antibody in a simple dilution test.

In a further aspect of the present invention there are provided test kits for use in carrying out the assay of the invention characterised in that they comprise a peptide, peptide-conjugate or antibodies of the invention, together with optional agents and items necessary for performing such assays. Such agents and items may include other binding agents or colour forming agents such as labelled antibodies, eg. biotinylated anti-horse IgG, horseradish peroxidase, streptavidin-peroxidase conjugate and o-phenylenediamine dihydrochloride. It will be realised that the term peptide and peptide conjugate as used herein will encompass oligopeptides, polypeptides and proteins as long as they fulfil the criteria of the invention with regard to immunological activity and content of epitopic sequences. The term 'conjugate' designates conjugation to any physiologically acceptable entity.

The peptides, peptide conjugates and binding assays of the present invention will now be described by way of example only by reference to the following sequence listing, figures and examples.

SEQUENCE LISTING:

SEQ ID No 1: is the DNA sequence equivalent to the entire EAV genome minus the first 18 bases and the polyA tail.

SEQ ID No 2: is the amino acid sequence corresponding to amino acids 1 to 137 of the EAV $G_L$ protein (including any signal sequence).

SEQ ID No 3: is the amino acid sequence corresponding to amino acids 19 to 137 of the EAV $G_L$ protein.

SEQ ID No 4: is the amino acid sequence corresponding to amino acids 28 to 137 of the EAV $G_L$ protein.

SEQ ID No 5: is the amino acid sequence corresponding to amino acids 75 to 97 of the EAV $G_L$ protein.

SEQ ID No 6: is the amino acid sequence that is fused with GST in Fp5.RsaI and used in the ELISA of Example 3.

SEQ ID No 7: is the amino acid sequence corresponding to the epitope at $G_L$ 85 to 97.

BRIEF DESCRIPTION OF DRAWINGS

FIG. 1: shows a graph relating $A_{490}$ values obtained using an Fp5.RsaI fusion protein ELISA carried out as described in Example 3 with VN derived results on the samples from the same horses.

FIG. 2: shows a graph relating $A4_{90}$ values obtained using an Sp25 ELISA carried out as described in Example 3 with VN derived results on samples from the same horses.

EXAMPLE 1: Production of peptides and conjugates of the invention and DNA and vectors encoding therefor.

cDNA encompassing EAV open reading frames (ORFs) 2 to 7 (as referred to by De Vries et al, 1992) corresponding to EAV proteins $G_s$, 3, 4, $G_L$, M and N were cloned into the bacterial expression vectors pGEX-3X and pGEX-2T (Table 1) and constructs screened for fusion protein expression using PAGE with cloning confirmed by RE digestion analysis and sequencing over the plasmid/insert junctions. Affinity purified glutathione-S-transferase (GST) fusion proteins were screened for reactivity by indirect ELISA with a panel of virus neutralising equine sera. Of the six fusion proteins (Fp2.0–Fp7.0) screened by this ELISA only Fp5. (see SEQ ID No 2 for EAV peptide content), corresponding to amino acids 28–137 of EAV $G_L$ plus GST reacted strongly with the neutralising sera. A panel of 96 neutralising and 96 non-neutralising sera were then tested by indirect ELISA against Fp5.0Amongst the virus neutralising sera tested 96/96 produced an $A_{490}$ greater than 0.4 aginst Fp5.0 in the ELISA with absorbance readings exhibiting a linear correlation to virus neutralising antibody titres (FIG. 1). 12/96 of the the neutralising equine sera tested positive to Fp5.0 in this ELISA.

Additional cloning experiments were performed with ORF 5 to produce fusion products 5.1, 5.2 and 5.4 which were affinity purified prior to testing with ELISA. Although Fp5.2 from this series of constructs was overexpressed during culture it proved difficult to affinity purify so a further round of cloning was performed to produce FP5.RsaI.

TABLE 1

EAV expression clone data:

| ORF | Fp | Vector pGEX Digest | SEQ ID No 1 | EAV Digest |
|---|---|---|---|---|
| 2 | 2.0 | 2T xSmaI*EcoRI | 10007–11476 | BalI-EcoRI |
| 3 | 3.0 | 3X xSmaI | 10310–10708 | HaeIII |
| 4 | 4.0 | 3X xBamHI*EcoRI | 10688–11205 | BglII-EcoRI$^V$ |
| 5 | 5.0 | 3X xSmaI | 11210–11538 | HaeII$^B$-ScaI |
| 6 | 6.0 | 3X xEcoRI$^B$ | 11897–12380 | HinfI$^B$-FspI |
| 7 | 7.0 | 3X xSmaI | 12287–12687 | HindIII$^V$ |
| 5 | 5.1 | 3X xSmaI | 11114–11291 | RsaI |
| 5 | 5.2 | 3X xSmaI | 11240–11475 | Sau3AI$^B$-EcoRI |
| 5 | 5.4 | 3X xEcoRI$^B$ | 11739–11876 | PvuII |
| 5 | 5.RsaI | 3X xEcoRI$^B$ | 11292–11423 | RsaI |

V=vector derived RE digestion site B=fragment/vector made blunt with Klenow DNA polymerase and T4 polymerase.

Peptide Sp25 (SEQ ID No 5) was also directly synthesised corresponding to the amino acid sequence of equine arteritis virus $G_L$ protein amino acid 75 to 97 and this and the product of Fp5.RSaI were tested with the ELISA as described in Example 3 (see FIG. 1 and 2). Fp5.RsaI was subsequently used in ELISA tests during the UK EAV outbreak in June 1993 to rapidly screen sera (Table 2) and used to test 1264 equine sera from a serosurvey carried out on Italian stallions (Table 3).

EXAMPLE 2: Immunisation studies.

Fp5.0, Fp5.RsaI and Sp25 were used to immunise rabbits and proved capable of inducing neutralising antibody response. Subsequent immunisation conducted on three groups of three horses confirmed Sp25 and Fp5.RsaI induce neutralising antibodies at a dose of 6 μg of EAV-specific peptide/conjugate agent for both groups. The peptide was delivered as an agent consisting of Sp25 coupled to keyhole limpet haemocyanin (KLH) and all vaccine doses were adjuvanted with Duphar polymer adjuvant at 0.5%. Doses were given at 0, 51 and 114 days; Sp25 and RsaI giving strong antibody production after each dose.

EXAMPLE 3: ELISA using Fp5.RsaI or Sp25 as binding agent.

Dynatech Immulon 3 microtitre plate wells were coated with Fp5.RsaI or Sp25 antigen by exposure to 100 μl of 5 μg/ml antigen in 0.05M carbonate buffer at pH9.6 (Sigma cat No C3041) at 4° C. overnight.

Plates were washed three times with Phosphate Buffered Saline (PBS) containing 0.05% Tween 20 (thereafter PBST) and then blocked with 100 μl PSBT containing 5% normal goat serum (Seralab) (thereafter PBSTG) for 1 hour at 37° C. Plates were washed again three times with PBST to render them ready for use.

Test sera were diluted 1:100 in PBSTG and 100 μl of this solution added to wells prepared as above and incubated for 90 minutes at 37° C. Plates were washed again three times with PBST and solution prepared by diluting 100 μl goat anti-horse IgG biotin conjugate (KPL catalog No 162102) 1:1000 in PBSTG and adding to each well before being incubated for 90 minutes at 37° C. Plates were washed three times with PSBT and a solution prepared by diluting 100 μl streptavidin-peroxidase conjugate (KPL catalog No 14-30-00) 1:1000 in PBSTG and adding to each well before incubating at room temperature for 30 minutes. Plates were washed three times with PBST and 100 μl o-phenylenediamine dihydro-chloride (Sigma cat No. P8287) (0.5 mg/ml in 0.05 phosphate citrate buffer, pH5.0-Sigma cat No. P4922) added to each well and incubated for 10 minutes at room temperature. 50 μl 4M $H_2SO_4$ was added to stop the reaction and absorbance was read at 490 nm. Since horse sera at a 1:100 dilution can bind native GST it is necessary to subtract absorbance readings obtained for sera against GST from GST-fusion protein absorbance. Each serum sample is tested in duplicate wells against each antigen. In each ELISA test 8 EAV VN positive sera and 8 EAV VN negative sera were run as internal controls.

TABLE 2

| EAV outbreak 1993-Fp5.RsaI ELISA vs VN results. | |
|---|---|
| ELISA positive VN negative | 46 (on 32 animals) |
| ELISA negative VN positive | 1 |
| ELISA positive VN positive | 148 |
| ELISA negative VN negative | 374 |
| ELISA and VN detected 17 animals that were seroconverters | |

TABLE 3

| Italian stallions 1993-Fp5.RsaI vs VN results | |
|---|---|
| ELISA positive VN negative | 369 |
| ELISA negative VN positive | 21 |
| ELISA positive VN positive | 441 |
| ELISA negative VN negative | 433 |

Samples assigned as ELISA positive if $A_{490}$ is over 0.15 16/21 of the ELISA negative VN positives had VN titres below 1/16.

I claim:

1. A peptide or peptide conjugate of the equine arteritis virus $G_L$ protein which elicits an immune response in animals to whom the peptide or peptide conjugate is administered and results in the production of neutralizing antibodies against equine arteritis virus, wherein said peptide or peptide conjugate is selected from the group consisting of SEQ ID NOs:3, 4, 5, 6 and 7.

2. A peptide of claim 1 wherein the peptide is SEQ ID NO:3 of the $G_L$ protein.

3. A peptide of claim 1 wherein the peptide is SEQ ID NO:4 of the $G_L$ protein.

4. A peptide of claim 1 wherein the peptide is SEQ ID NO:5 of the $G_L$ protein.

5. A peptide of claim 1 wherein the peptide is SEQ ID NO:6 of the $G_L$ protein.

6. A peptide of claim 1 wherein the peptide is SEQ ID NO:7 of the $G_L$ protein.

7. A diagnostic agent for the detection of equine arteritis virus, said agent comprising a peptide or peptide conjugate which elicits an immune response in animals to whom the peptide or peptide conjugate is administered, and results in the production of neutralizing antibodies against equine arteritis virus, said peptide or peptide conjugate is selected from the group consisting of SEQ ID NOs:3, 4, 5, 6 and 7.

8. A method for testing for the presence or amount of antibodies to equine arteritis virus present in the sample comprising binding a peptide or peptide conjugate of claim 1 to the antibodies in said sample and detecting binding of said antibodies to said peptide or peptide conjugate, wherein said binding indicates the presence or amount of antibodies to equine arteritis virus.

9. A method of claim 8 wherein the binding occurs in an ELISA or radioimmunoassay (RIA) assay.

10. A method of claim 8 or 9 wherein the peptide or peptide conjugate is immobilized upon an assay plate and is used to bind equine arteritis virus specific antibodies present in the sample.

11. A method of claim 8 or 9 wherein the peptide or peptide conjugate is detectably labeled and is used to identify equine arteritis virus specific antibodies that have been immobilized onto an assay plate, said method comprising exposing the plate immobilized antibodies to the labeled peptide or peptide conjugate, measuring the amount of label bound to the plate thereafter, and relating the amount of label to the presence or amount of antibodies in the sample.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
( A ) LENGTH: 12687 base pairs
( B ) TYPE: nucleic acid
( C ) STRANDEDNESS: single
( D ) TOPOLOGY: unknown ( i i ) MOLECULE TYPE: cDNA ( x i ) SEQUENCE DESCRIPTION: SEQ ID NO: 1:

```
TGCCATATAC GGCTCACCAC CATATACACT GCAAGAATTA CTATTCTTGT GGGCCCCTCT    60
CGGTAAATCC TAGAGGGCTT TCCTCTCGTT ATTGCGAGAT TCGTCGTTAG ATAACGGCAA   120
GTTCCCTTTC TTACTATCCT ATTTTCATCT TGTGGCTTGA CGGGTCACTG CCATCGTCGT   180
CGATCTCTAT CAACTACCCT TGCGACTATG GCAACCTTCT CCGCTACTGG ATTTGGAGGG   240
AGTTTTGTTA GGGACTGGTC CCTGGACTTA CCCGACGCTT GTGAGCATGG CGCGGGATTG   300
TGCTGCGAAG TGGACGGCTC CACCTTATGC GCCGAGTGTT TTCGCGGTTG CGAAGGAATG   360
GAGCAATGTC CTGGCTTGTT CATGGGACTG TTAAAACTGG CTTCGCCAGT TCCAGTGGGA   420
CATAAGTTCC TGATTGGTTG GTATCGAGCT GCCAAAGTCA CCGGGCGTTA CAATTTCCTT   480
GAGCTGTTGC AACACCCTGC TTTCGCCCAG CTGCGTGTGG TTGATGCTAG GTTAGCCATT   540
```

```
GAAGAGGCAA  GTGTGTTTAT  TTCCACTGAC  CACGCGTCTG  CTAAGCGTTT  CCCTGGCGCT    600
AGATTTGCGC  TGACACCGGT  GTATGCTAAC  GCTTGGGTTG  TGAGCCCGGC  TGCTAACAGT    660
TTGATAGTGA  CCACTGACCA  GGAACAAGAT  GGGTTCTGCT  GGTTAAAACT  TTTGCCACCT    720
GACCGCCGTG  AGGCTGGTTT  GCGGTTGTAT  TACAACCATT  ACCGCGAACA  AAGGACCGGG    780
TGGCTGTCTA  AAACAGGACT  TCGCTTATGG  CTTGGAGACC  TGGGTTTGGG  CATCAATGCG    840
AGCTCTGGAG  GGCTGAAATT  CCACATTATG  AGGGGTTCGC  CTCAGCGAGC  TTGGCATATC    900
ACAACACGCA  GCTGCAAGCT  GAAGAGCTAC  TACGTTTGTG  ACATCTCTGA  AGCAGACTGG    960
TCCTGTTTGC  CTGCTGGCAA  CTACGGCGGC  TACAATCCAC  CAGGGGACGG  AGCTTGCGGT   1020
TACAGGTGCT  TGGCCTTCAT  GAATGGCGCC  ACTGTTGTGT  CGGCTGGTTG  CAGTTCTGAC   1080
TTGTGGTGTG  ATGATGAGTT  GGCTTATCGA  GTCTTTCAAT  TGTCACCCAC  GTTCACGGTT   1140
ACCATCCCAG  GTGGGCGAGT  TTGTCCGAAT  GCCAAGTACG  CAATGATTTG  TGACAAGCAG   1200
CACTGGCGCG  TCAAACGTGC  AAAGGGCGTC  GGCCTGTGTC  TCGATGAAAG  CTGTTTCAGG   1260
GGCATCTGCA  ATTGCCAACG  CATGAGTGGA  CCACCACCTG  CACCCGTGTC  AGCCGCCGTG   1320
TTAGATCACA  TACTGGAGGC  GGCGACGTTT  GGCAACGTTC  GCGTGGTTAC  ACCTGAAGGG   1380
CAGCCACGCC  CCGTACCAGC  GCCGCGAGTT  CGTCCCAGCG  CCAACTCTTC  TGGAGATGTC   1440
AAAGATCCGG  CGCCCGTTCC  GCCAGTACCA  AAACCAAGGA  CCAAGCTTGC  CACACCGAAC   1500
CCAACTCAGG  CGCCCATCCC  AGCACCGCGC  ACGCGACTTC  AAGGGGCCTC  AACACAGGAG   1560
CCACTGGCGA  GTGCAGGAGT  TGCTTCTGAC  TCGGCACCTA  AATGGCGTGT  GGCCAAAACT   1620
GTGTACAGCT  CCGCGGAGCG  CTTTCGGACC  GAACTGGTAC  AACGTGCTCG  GTCCGTTGGG   1680
GACGTTCTTG  TTAAGCGCT   ACCGCTCAAA  ACCCCAGCAG  TGCAGCGGTA  TACCATGACT   1740
CTGAAGATGA  TGCGTTCACG  CTTCAGTTGG  CACTGCGACG  TGTGGTACCC  TTTGGCTGTA   1800
ATCGCTTGTT  TGCTCCCTAT  ATGGCCATCT  CTTGCTTTGC  TCCTTAGCTT  TGCCATTGGG   1860
TTGATACCCA  GTGTGGGCAA  TAATGTTGTT  CTGACAGCGC  TTCTGGTTTC  ATCAGCTAAT   1920
TATGTTGCGT  CAATGGACCA  TCAATGTGAA  GGTGCGGCTT  GCTTAGCCTT  GCTGGAAGAA   1980
GAACACTATT  ATAGAGCGGT  CCGTTGGCGC  CCGATTACAG  GCGCGCTGTC  GCTTGTGCTC   2040
AATTTACTGG  GGCAGGTAGG  CTATGTAGCT  CGTTCCACCT  TTGATGCAGC  TTATGTTCCT   2100
TGCACTGTGT  TCGATCTTTG  CAGCTTTGCT  ATTCTGTACC  TCTGCCGCAA  TCGTTGCTGG   2160
AGATGCTTCG  GACGCTGTGT  GCGAGTTGGG  CCTGCCACGC  ATGTTTGGG   CTCCACCGGG   2220
CAACGAGTTT  CCAAACTGGC  GCTCATTGAT  TTGTGTGACC  ACTTTTCAAA  GCCCACCATC   2280
GATGTTGTGG  GCATGGCAAC  TGGTTGGAGC  GGATGTTACA  CAGGAACCGC  CGCAATGGAG   2340
CGTCAGTGTG  CCTCTACGGT  GGACCCTCAC  TCGTTCGACC  AGAAGAAGGC  AGGAGCGACT   2400
GTTTACCTCA  CCCCCCCTGT  CAACAGCGGG  TCAGCGCTGC  AGTGCCTCAA  TGTCATGTGG   2460
AAGCGACCAA  TTGGGTCCAC  TGTCCTTGGG  GAACAAACAG  GAGCTGTTGT  GACGGCGGTC   2520
AAGAGTATCT  CTTTCTCACC  TCCCTGCTGC  GTCTCTACCA  CTTTGCCCAC  CGACCCGGT    2580
GTGACCGTTG  TCGACCATGC  TCTTTACAAC  CGGTTGACTG  CTTCAGGGGT  CGATCCCGCT   2640
TTATTGCGTG  TTGGGCAAGG  TGATTTTCTA  AAACTTAATC  CGGGGTTCCG  GCTGATAGGT   2700
GGATGGATTT  ATGGGATATG  CTATTTTGTG  TTGGTGGTTG  TGTCAACTTT  TACCTGCTTA   2760
CCTATCAAAT  GTGGCATTGG  CACCCGCGAC  CCTTTCTGCC  GCAGAGTGTT  TTCTGTACCC   2820
GTCACCAAGA  CCCAAGAGCA  CTGCCATGCT  GGAATGTGTG  CTAGCGCTGA  AGGCATCTCT   2880
CTGGACTCTC  TGGGGTTAAC  TCAGTTACAA  AGTTACTGGA  TCGCAGCCGT  CACTAGCGGA   2940
```

| | | | | | |
|---|---|---|---|---|---|
|TTAGTGATCT|TGTTGGTCTG|CCACCGCCTG|GCCATCAGCG|CCTTGGACTT|GTTGACTCTA 3000|
|GCTTCCCCTT|TAGTGTTGCT|TGTGTTCCCT|TGGGCATCTG|TGGGGCTTTT|ACTTGCTTGC 3060|
|AGTCTCGCTG|GTGCTGCTGT|GAAAATACAG|TTGTTGGCGA|CGCTTTTTGT|GAATCTGTTC 3120|
|TTTCCCCAAG|CTACCCTTGT|CACTATGGGA|TACTGGGCGT|GCGTGGCGGC|TTTGGCCGTT 3180|
|TACAGTTTGA|TGGGCTTGCG|AGTGAAAGTG|AATGTGCCCA|TGTGTGTGAC|ACCTGCCCAT 3240|
|TTTCTGCTGC|TGGCGAGGTC|AGCTGGACAG|TCAAGAGAGC|AGATGCTCCG|GGTCAGCGCT 3300|
|GCTGCCCCCA|CCAATTCACT|GCTTGGAGTG|GCTCGTGATT|GTTATGTCAC|AGGCACAACT 3360|
|CGGCTGTACA|TACCCAAGGA|AGGCGGGATG|GTGTTTGAAG|GGCTATTCAG|GTCACCGAAG 3420|
|GCGCGCGGCA|ACGTCGGCTT|CGTGGCTGGT|AGCAGCTACG|GCACAGGGTC|AGTGTGGACC 3480|
|AGGAACAACG|AGGTCGTCGT|ACTGACAGCG|TCACACGTGG|TTGGCCGCGC|TAACATGGCC 3540|
|ACTCTGAAGA|TCGGTGACGC|AATGCTGACT|CTGACTTTCA|AAAGAATGG|CGACTTCGCC 3600|
|GAGGCAGTGA|CGACACAGTC|CGAGCTCCCA|GGCAATTGGC|CACAGTTGCA|TTTCGCCCAA 3660|
|CCAACAACCG|GGCCCGCTTC|ATGGTGCACT|GCCACAGGAG|ATGAAGAAGG|CTTGCTCAGT 3720|
|GGCGAGGTTT|GTCTGGCGTG|GACTACTAGT|GGCGACTCTG|GATCTGCAGT|GGTTCAGGGT 3780|
|GACGCTGTGG|TAGGGGTCCA|CACCGGTTCG|AACACAAGTG|GTGTTGCCTA|CGTGACCACC 3840|
|CCAAGCGGAA|AACTCCTTGG|CGCCGACACC|GTGACTTTGT|CATCACTGTC|AAAGCATTTC 3900|
|ACAGGCCCTT|TGACATCAAT|CCCGAAGGAC|ATCCCTGACA|ACATTATTGC|CGATGTTGAT 3960|
|GCTGTTCCTC|GTTCTCTGGC|CATGCTGATT|GATGGCTTAT|CCAATAGAGA|GAGCAGCCTT 4020|
|TCTGGACCTC|AGTTGTTGTT|AATTGCTTGT|TTATGTGGT|CTTATCTTAA|CCAACCTGCT 4080|
|TACTTGCCTT|ATGTGCTGGG|CTTCTTTGCC|GCTAACTTCT|TCCTGCCAAA|AAGTGTTGGC 4140|
|CGCCCTGTGG|TCACTGGGCT|TCTATGGTTG|TGCTGCCTCT|TCACACCGCT|TTCCATGCGC 4200|
|TTGTGCTTGT|TCCATCTGGT|CTGTGCTACC|GTCACGGGAA|ACGTGATATC|TTTGTGGTTC 4260|
|TACATCACTG|CCGCTGGCAC|GTCTTACCTT|TCTGAGATGT|GGTTCGGAGG|CTATCCCACC 4320|
|ATGTTGTTTG|TGCCACGGTT|CCTAGTGTAC|CAGTTCCCCG|GCTGGGCTAT|TGGCACAGTA 4380|
|CTAGCGGTAT|GCAGCATCAC|CATGCTGGCT|GCTGCCCTCG|GTCACACCCT|GTTACTGGAT 4440|
|GTGTTCTCCG|CCTCAGGTCG|CTTTGACAGG|ACTTTCATGA|TGAAATACTT|CCTGGAGGGA 4500|
|GGAGTGAAAG|AGAGTGTCAC|CGCCTCAGTC|ACCCGCGCTT|ATGGCAAACC|AATTACCCAG 4560|
|GAGAGTCTCA|CTGCAACATT|AGCTGCCCTC|ACTGATGATG|ACTTCCAATT|CCTCTCTGAT 4620|
|GTGCTTGACT|GTCGGGCCGT|CCGATCGGCA|ATGAATCTCG|GTGCCGCTCT|CACAAGTTTT 4680|
|CAAGTGGCGC|AGTATCGTAA|CATCCTTAAT|GCATCCTTGC|AAGTCGATCG|TGACGCTGCT 4740|
|CGTAGTCGCA|GACTAATGGC|AAAACTGGCT|GATTTTGCGG|TTGAACAAGA|AGTAACAGCT 4800|
|GGAGACCGTG|TTGTGGTTAT|CGACGGTCTG|GACCGCATGG|CTCACTTCAA|AGACGATTTG 4860|
|GTGCTGGTTC|CTTTGACCAC|CAAAGTAGTA|GGCGGTTCTA|GGTGCACCAT|TTGTGACGTC 4920|
|GTTAAGGAAG|AAGCCAATGA|CACCCAGTT|AAGCCAATGC|CCAGCAGGAG|ACGCCGCAAG 4980|
|GGCCTGCCTA|AAGGTGCTCA|GTTGGAGTGG|GACCGTCACC|AGGAAGAGAA|GAGGAACGCC 5040|
|GGTGATGATG|ATTTTGCGGT|CTCGAATGAT|TATGTCAAGA|GAGTGCCAAA|GTACTGGGAT 5100|
|CCCAGCGACA|CCCGAGGCAC|GACAGTGAAA|ATCGCCGGCA|CTACCTATCA|GAAAGTGGTT 5160|
|GACTATTCAG|GCAATGTGCA|TTACGTGGAG|CATCAGGAAG|ATCTGCTAGA|CTACGTGCTG 5220|
|GGCAAGGGGA|GCTATGAAGG|CCTAGATCAG|GACAAAGTGT|TGGACCTCAC|AAACATGCTT 5280|
|AAAGTGGACC|CCACGGAGCT|CTCCTCCAAA|GACAAAGCCA|AGGCGCGTCA|CGTTGCTCAT 5340|

```
CTGCTGTTGG ATCTGGCTAA CCCAGTTGAG GCAGTGAATC AGTTAAACTG AGAGCGCCCC    5400
ACATCTTTCC CGGCGATGTG GGGCGTCGGA CCTTTGCTGA CTCTAAAGAC AAGGGTTTCG    5460
TGGCTCTACA CAGTCGCACA ATGTTTTAG  CTGCCCGGGA CTTTTTATTT AACATCAAAT    5520
TTGTGTGCGA CGAAGAGTTC ACAAGACCC  CAAAAGACAC ACTGCTTGGG TACGTACGCG    5580
CCTGCCCTGG TTACTGGTTT ATTTTCCGTC GTACGCACCG GTCGCTGATT GATGCATACT    5640
GGGACAGTAT GGAGTGCGTT TACGCGCTTC CCACCATATC TGATTTTGAT GTGAGCCCAG    5700
GTGACGTCGC AGTGACGGGC GAGCGATGGG ATTTTGAATC TCCCGGAGGA GGCCGTGCAA    5760
AACGTCTCAC AGCTGATCTG GTGCACGCTT TTCAAGGGTT CCACGGAGCC TCTTATTCCT    5820
ATGATGACAA GGTGGCAGCT GCTGTCAGTG GTGACCCGTA TCGGTCGGAC GGCGTCTTGT    5880
ATAACACCCG TTGGGGCAAC ATTCCATATT CTGTCCCAAC CAATGCTTTG GAAGCCACAG    5940
CTTGCTACCG TGCTGGATGT GAGGCCGTTA CCGACGGGAC CAACGTCATC GCAACAATTG    6000
GGCCCTTCCC GGAGCAACAA CCCATACCGG ACATCCCAAA GAGCGTGCTT GACAACTGCG    6060
CTGACATCAG CTGTGACGCT TTCATAGCGC CCGCTGCAGA GACAGCCCTG TGTGGAGATT    6120
TAGAGAAATA CAACCTATCC ACGCAGGGTT TTGTGTTGCC TAGTGTTTTC TCCATGGTGC    6180
GGGCGTACTT AAAAGAGGAG ATTGGAGACG CTCCACCACT CTACTTGCCA TCTACTGTAC    6240
CATCTAAAAA TTCACAAGCC GGAATTAACG GCGCTGAGTT TCCTACAAAG TCTTTACAGA    6300
GCTACTGTTT GATTGATGAC ATGGTGTCAC AGTCCATGAA AAGCAATCTA CAAACCGCCA    6360
CCATGGCGAC TTGTAAACGG CAATACTGTT CCAAATACAA GATTAGGAGC ATTCTGGGCA    6420
CCAACAATTA CATTGGCCTA GGTTTGCGTG CCTGCCTTTC GGGGGTTACG GCCGCATTCC    6480
AAAAAGCTGG AAAGGATGGG TCACCGATTT ATTTGGGCAA GTCAAAATTC GACCCGATAC    6540
CAGCTCCTGA CAAGTACTGC CTTGAAACAG ACCTGGAGAG TTGTGATCGC TCCACCCCGG    6600
CTTTGGTGCG TTGGTTCGCT ACTAATCTTA TTTTTGAGCT AGCTGGCCAG CCCGAGTTGG    6660
TGCACAGCTA CGTGTTGAAT TGCTGTCACG ATCTAGTTGT GGCGGGTAGT GTAGCATTCA    6720
CCAAACGCGG GGGTTTGTCA TCTGGAGACC CTATCACTTC CATTTCCAAT ACCATCTATT    6780
CATTGGTGCT GTACACCCAG CACATGTTGC TATGTGGACT TGAAGGCTAT TTCCCAGAGA    6840
TTGCAGAAAA ATATCTTGAT GGCAGCCTGG AGCTGCGGGA CATGTTCAAG TACGTTCGAG    6900
TGTACATCTA CTCGGACGAT GTGGTTCTAA CCACACCCAA CCAGCATTAC GCGGCCAGCT    6960
TTGACCGCTG GGTCCCCCAC CTGCAGGCGC TGCTAGGTTT CAAGGTTGAC CCAAAGAAAA    7020
CTGTGAACAC CAGCTCCCCT TCCTTTTTGG GCTGCCGGTT CAAGCAAGTG GACGGCAAGT    7080
GTTATCTAGC CAGTCTTCAG GACCGCGTTA CACGCTCTCT GTTATACCAC ATTGGTGCAA    7140
AGAATCCCTC AGAGTACTAT GAAGCTGCTG TTTCCATCTT TAAGGACTCC ATTATCTGCT    7200
GTGATGAAGA CTGGTGGACG GACCTCCATC GACGTATCAG TGGCGCTGCG CGTACCGACG    7260
GAGTTGAGTT CCCCACCATT GAAATGTTAA CATCCTTCCG CACCAAGCAG TATGAGAGTG    7320
CCGTGTGCAC AGTTTGTGGG GCCGCCCCCG TGGCCAAGTC TGCTTGTGGA GGGTGGTTCT    7380
GTGGCAATTG TGTCCCGTAC CACGCGGGTC ATTGTCACAC AACCTCGCTC TTCGCCAACT    7440
GCGGGCACGA CATCATGTAC CGCTCCACTT ACTGCACAAT GTGTGAGGGT TCCCCAAAAC    7500
AGATGGTACC AAAAGTGCCT CACCCGATCC TGGATCATTT GCTGTGCCAC ATTGATTACG    7560
GCAGTAAAGA GGAACTAACT CTGGTAGTGG CGGATGGTCG AACAACATCA CCGCCCGGGC    7620
GCTACAAAGT GGGTCACAAG GTAGTCGCCG TGGTTGCAGA TGTGGGAGGC AACATTGTGT    7680
TTGGGTGCGG TCCTGGATCA CACATCGCAG TACCACTTCA GGATACGCTC AAGGGCGTGG    7740
```

```
TGGTGAATAA AGCTCTGAAG AACGCCGCCG CCTCTGAGTA CGTGGAAGGA CCCCCTGGGA    7800
GTGGGAAGAC TTTTCACCTG GTCAAAGATG TGCTAGCCGT GGTCGGTAGC GCGACCTTGG    7860
TTGTGCCCAC CCACGCGTCC ATGCTGGACT GCATCAACAA GCTCAAACAA GCGGGCGCCG    7920
ATCCATACTT TGTGGTGCCC AAGTATACAG TTCTTGACTT TCCCCGGCCT GGCAGTGGAA    7980
ACATCACAGT GCGACTGCCA CAGGTCGGAA CCAGTGAGGG AGAAACCTTT GTGGATGAGG    8040
TGGCCTACTT CTCACCAGTG GATCTGGCGC GCATTTAAC CCAGGGTCGA GTCAAGGGTT    8100
ACGGTGATTT AAATCAGCTC GGGTGCGTCG GACCCGCGAG CGTGCCACGT AACCTTTGGC    8160
TCCGACATTT TGTCAGCCTG GAGCCCTTGC GAGTGTGCCA TCGATTCGGC GCTGCTGTGT    8220
GTGATTTGAT CAAGGGCATT TATCCTTATT ATGAGCCAGC TCCACATACC ACTAAAGTGG    8280
TGTTTGTGCC AAATCCAGAC TTTGAGAAAG GTGTAGTCAT CACCGCCTAC CACAAAGATC    8340
GCGGTCTTGG TCACCGCACA ATTGATTCAA TTCAAGGCTG TACATTCCCT GTTGTGACTC    8400
TTCGACTGCC CACACCCCAA TCACTGACGC GCCCGCGCGC AGTTGTGGCG GTTACTAGGG    8460
CGTCTCAGGA ATTATACATC TACGACCCCT TGATCAGCT TAGCGGGTTG TTGAAGTTCA    8520
CCAAGGAAGC AGAGGCGCAG GACTTGATCC ATGGCCCACC TACAGCATGC CACCTGGGCC    8580
AAGAAATTGA CCTTTGGTCC AATGAGGGCC TCGAATATTA CAAGGAAGTC AACCTGCTGT    8640
ACACACACGT CCCCATCAAG GATGGTGTAA TACACAGTTA CCCTAATTGT GGCCCTGCCT    8700
GTGGCTGGGA AAAGCAATCC AACAAAATTT CGTGCCTCCC GAGAGTGGCA CAAAATTTGG    8760
GCTACCACTA TTCCCCAGAC TTACCAGGAT TTTGCCCCAT ACCAAAAGAA CTCGCTGAGC    8820
ATTGGCCCGT AGTGTCCAAT GATAGATACC CGAATTGCTT GCAAATTACC TTACAGCAAG    8880
TATGTGAACT CAGTAAACCG TGCTCAGCGG GCTATATGGT TGGACAATCT GTTTTCGTGC    8940
AGACGCCTGG TGTGACATCT TACTGGCTTA CTGAATGGGT CGACGGCAAA GCGCGTGCTC    9000
TACCAGATTC CTTATTCTCG TCCGGTAGGT TCGAGACTAA CAGCCGCGCT TCCTCGATG    9060
AAGCCGAGGA AAAGTTTGCC GCCGCTCACC CTCATGCCTG TTTGGGAGAA ATTAATAAGT    9120
CCACCGTGGG AGGATCCCAC TTCATCTTTT CCCAATATTT ACCACCATTG CTACCCGCAG    9180
ACGCTGTTGC CCTGGTAGGT GCTTCATTGG CTGGGAAAGC TGCTAAAGCT GCTTGCAGCG    9240
TTGTTGATGT CTATGCTCCA TCATTTGAAC CTTATCTACA CCCTGAGACA CTGAGTCGCG    9300
TGTACAAGAT TATGATCGAT TTCAAGCCGT GTAGGCTTAT GGTGTGGAGA AACGCGACCT    9360
TTTATGTCCA AGAGGGTGTT GATGCAGTTA CATCAGCACT AGCAGCTGTG TCCAAACTCA    9420
TCAAAGTGCC GGCCAATGAG CCTGTTTCAT TCCATGTGGC ATCAGGGTAC AGAACCAACG    9480
CGCTGGTAGC GCCCCAGGCT AAAATTTCAA TTGGAGCCTA CGCCGCCGAG TGGGCACTGT    9540
CAACTGAACC GCCACCTGCT GGTTATGCGA TCGTGCGGCG ATATATTGTA AAGAGGCTCC    9600
TCAGCTCAAC AGAAGTGTTC TTGTGCCGCA GGGGTGTTGT GTCTTCCACC TCAGTGCAGA    9660
CCATTTGTGC ACTAGAGGGA TGTAAACCTC TGTTCAACTT CTTACAAATT GGTTCAGTCA    9720
TTGGGCCCGT GTGATGGGCT TAGTGTGGTC ACTGATTTCA AATTCTATTC AGACTATTAT    9780
TGCTGATTTT GCTATTTCTG TGATTGATGC AGCGCTTTTC TTTCTCATGC TACTTGCATT    9840
GGCTGTTGTT ACTGTGTTTC TTTTCTGGCT CATTGTTGCC ATCGGCCGCA GCTTGGTGGC    9900
GCGGTGTTCA CGAGGTGCGC GTTACAGACC TGTTTAAGGA TTTGCAGTGC GACAACCTGC    9960
GCGCGAAAGA TGCCTTCCCG AGTCTGGGAT ATGCTCTGTC GATTGGCCAG TCGAGGCTAT   10020
CGTATATGCT GCAGGATTGG TTGCTTGCTG CGCACCGCAA GGAAGTTATG CCTTCCAATA   10080
TCATGCCTAT GCCCGGTCTT ACTCCTGATT GCTTTGACCA TCTGGAGTCT TCTAGCTATG   10140
```

```
CTCCATTTAT CAATGCCTAT CGGCAGGCAA TTTTGAGTCA ATACCCACAA GAGCTCCAGC    10200

TCGAAGCCAT CAACTGTAAA TTGCTTGCTG TGGTTGCACC GGCATTGTAT CATAATTACC    10260

ATCTAGCCAA TTTGACCGGA CCGGCCACAT GGGTCGTGCC TACAGTGGGC CAGTTGCACT    10320

ATTATGCTTC TTCCTCTATT TTTGCTTCAT CTGTGGAAGT GTTGGCAGCA ATAATACTAC    10380

TATTTGCATG CATACCACTA GTGACACGAG TGTACATCTC TTTTACGCGG CTAATGTCAC    10440

CTTCCCGTCG CACTTCCAGC GGCACTTTGC CGCGGCGCAA GATTTTGTAG TGCACACGGG    10500

TTATGAATAT GCCGGGGTCA CTATGTTAGT GCACTTGTTT GCCAACTTGG TTCTGACATT    10560

TCCGAGCTTA GTTAATTGTT CCCGCCCTGT GAATGTCTTT GCTAATGCTT CTTGCGTGCA    10620

AGTGGTTTGT AGTCATACCA ACTCAACTAC TGGCTTGGGT CAACTTTCTT TTTCCTTTGT    10680

AGATGAAGAT CTACGGCTGC ATATCAGGCC TACTCTTATT TGTTGGTTTG CCTTGTTGTT    10740

GGTGCACTTT CTACCCATGC CACGCTGCAG AGGCTCGTAA TTTTACTTAC ATTAGTCATG    10800

GATTGGGCCA CGTGCACGGT CATGAGGGGT GTAGGAATTT TATTAATGTC ACTCATTCTG    10860

CATTTCTTTA TCTTAATCCC ACCACTCCCA CTGCGCCGGC TATAACTCAT TGTTTACTTC    10920

TGGTTCTGGC AGCCAAAATG GAACACCCAA ACGCTACTAT CTGGCTGCAG CTGCAGCCGT    10980

TTGGGTATCA TGTGGCTGGC GATGTCATTG TCAACTTGGA AGAGGACAAG AGGCATCCTT    11040

ACTTTAAACT TTTGAGAGCG CCGGCTTTAC CGCTTGGTTT TGTGGCTATA GTTTATGTTC    11100

TTTTACGACT GGTACGTTGG GCTCAACG ATG TTA TCT ATG ATT GTA TTG CTA       11152
                               Met Leu Ser Met Ile Val Leu Leu
                                1                   5

TTC TTG CTT TGG GGT GCG CCA TCA CAT GCT TAC TTC TCA TAC TAC ACC      11200
Phe Leu Leu Trp Gly Ala Pro Ser His Ala Tyr Phe Ser Tyr Tyr Thr
    10              15                  20

GCT CAG CGC TTC ACA GAC TTC ACC TTG TGT ATG CTG ACG GAT CGC GGC      11248
Ala Gln Arg Phe Thr Asp Phe Thr Leu Cys Met Leu Thr Asp Arg Gly
 25              30                  35                  40

GTT ATT GCC AAT TTG CTG CGA TAT GAT GAG CAC ACT GCT TTG TAC AAT      11296
Val Ile Ala Asn Leu Leu Arg Tyr Asp Glu His Thr Ala Leu Tyr Asn
             45              50                  55

TGT TCC GCC AGT AAA ACC TGT TGG TAT TGC ACA TTC CTG GAC GAA CAG      11344
Cys Ser Ala Ser Lys Thr Cys Trp Tyr Cys Thr Phe Leu Asp Glu Gln
         60              65                  70

ATT ATC ACG TTT GGA ACC GAT TGT GAT GAC ACC TAC GCG GTC CCA GTT      11392
Ile Ile Thr Phe Gly Thr Asp Cys Asp Asp Thr Tyr Ala Val Pro Val
     75              80                  85

GCT GAG GTC CTG GAA CAG GCG CAT GGA CCG TAC AGT GCG CTG TTT GAT      11440
Ala Glu Val Leu Glu Gln Ala His Gly Pro Tyr Ser Ala Leu Phe Asp
 90              95                  100

GAC ATG CCC CCT TTT ATT TAC TAT GGC CGT GAA TTC GGC ATA GTT GTG      11488
Asp Met Pro Pro Phe Ile Tyr Tyr Gly Arg Glu Phe Gly Ile Val Val
105             110                 115                 120

TTG GAT GTG TTT ATG TTC TAT CCC GTT TTA GTT CTG TTT TTC TTA TCA      11536
Leu Asp Val Phe Met Phe Tyr Pro Val Leu Val Leu Phe Phe Leu Ser
            125                 130                 135

GTA CTACCCTATG CTACGCTTAT TCTTGAAATG TGTGTATCTA TTCTGTTTAT           11589
Val

AATCTATGGC ATTTACAGCG GGCCTACTT GGCCATGGGC ATATTTGCGG CCACGCTTGC     11649

TATACATTCA ATTGTGGTCC TCCGCCAATT ACTGTGGTTA TGCCTGGCTT GGCGATACCG    11709

CTGTACGCTT CACGCGTCCT TTATATCAGC TGAGGGGAAA GTGTACCCCG TAGACCCCGG    11769

ACTCCCGGTT GCCGCCGTGG GCAATCGGTT GTTAGTCCCA GGTAGGCCCA CTATCGATTA    11829
```

| | | | | | |
|---|---|---|---|---|---|
| TGCAGTGGCC | TACGGCAGCA | AAGTCAACCT | TGTGAGGTTG | GGGGCAGCTG | AGGTATGGGA | 11889
| GCCATAGATT | CATTTGTGG | TGACGGGATT | TTAGGTGAGT | ATCTAGATTA | CTTTATTCTG | 11949
| TCCGTCCCAC | TCTTGCTGTT | GCTTACTAGG | TATGTAGCAT | CTGGGTTAGT | GTATGTTTTG | 12009
| ACTGCCTTGT | TCTATTCCTT | TGTATTAGCA | GCTTATATTT | GGTTTGTTAT | AGTTGGAAGA | 12069
| GCCTTTTCTA | CTGCTTATGC | TTTTGTGCTT | TTGGCTGCTT | TTCTGTTATT | AGTAATGAGG | 12129
| ATGATTGTGG | GTATGATGCC | TCGTCTTCGG | TCCATTTTCA | ACCATCGCCA | ACTGGTGGTA | 12189
| GCTGATTTTG | TGGACACACC | TAGTGGACCT | GTTCCCATCC | CCCGCTCAAC | TACTCAGGTA | 12249
| GTGGTTCGCG | GCAACGGGTA | CACCGCAGTT | GGTAACAAGC | TTGTCGATGG | CGTCAAGACG | 12309
| ATCACGTCCG | CAGGCCGCCT | CTTTTCGAAA | CGGACGGCGG | CGACAGCCTA | CAAGCTACAA | 12369
| TGACCTACTG | CGCATGTTTG | GTCAGATGCG | GGTCCGCAAA | CCGCCCGCGC | AACCCACTCA | 12429
| GGCTATTATT | GCAGAGCCTG | GAGACCTTAG | GCATGATTTA | AATCAACAGG | AGCGCGCCAC | 12489
| CCTTTCGTCG | AACGTACAAC | GGTTCTTCAT | GATTGGGCAT | GGTTCACTCA | CTGCAGATGC | 12549
| CGGAGGACTC | ACGTACACCG | TCAGTTGGGT | TCCTACCAAA | CAAATCCAGC | GCAAAGTTGC | 12609
| GCCTCCAGCA | GGGCCGTAAG | ACGTGGATAT | TCTCCTGTGT | GGCGTCATGT | TGAAGTAGTT | 12669
| ATTAGCCACC | CAGGAACC | | | | | 12687

(2) INFORMATION FOR SEQ ID NO: 2:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Leu Ser Met Ile Val Leu Leu Phe Leu Leu Trp Gly Ala Pro Ser
 1               5                  10                  15
His Ala Tyr Phe Ser Tyr Tyr Thr Ala Gln Arg Phe Thr Asp Phe Thr
                20                  25                  30
Leu Cys Met Leu Thr Asp Arg Gly Val Ile Ala Asn Leu Leu Arg Tyr
            35                  40                  45
Asp Glu His Thr Ala Leu Tyr Asn Cys Ser Ala Ser Lys Thr Cys Trp
    50                  55                  60
Tyr Cys Thr Phe Leu Asp Glu Gln Ile Ile Thr Phe Gly Thr Asp Cys
65                  70                  75                  80
Asp Asp Thr Tyr Ala Val Pro Val Ala Glu Val Leu Glu Gln Ala His
                85                  90                  95
Gly Pro Tyr Ser Ala Leu Phe Asp Asp Met Pro Pro Phe Ile Tyr Tyr
            100                 105                 110
Gly Arg Glu Phe Gly Ile Val Val Leu Asp Val Phe Met Phe Tyr Pro
        115                 120                 125
Val Leu Val Leu Phe Phe Leu Ser Val
    130                 135
```

(2) INFORMATION FOR SEQ ID NO: 3:

(i) SEQUENCE CHARACTERISTICS:
        (A) LENGTH: 119 amino acids
        (B) TYPE: amino acid
        (D) TOPOLOGY: unknown (ii) MOLECULE TYPE: peptide (xi) SEQUENCE DESCRIPTION: SEQ ID NO: 3:

```
Tyr Phe Ser Tyr Tyr Thr Ala Gln Arg Phe Thr Asp Phe Thr Leu Cys
 1               5                  10                  15

Met Leu Thr Asp Arg Gly Val Ile Ala Asn Leu Leu Arg Tyr Asp Glu
             20              25                  30

His Thr Ala Leu Tyr Asn Cys Ser Ala Ser Lys Thr Cys Trp Tyr Cys
         35              40                  45

Thr Phe Leu Asp Glu Gln Ile Ile Thr Phe Gly Thr Asp Cys Asp Asp
     50              55                  60

Thr Tyr Ala Val Pro Val Ala Glu Val Leu Glu Gln Ala His Gly Pro
 65              70                  75                       80

Tyr Ser Ala Leu Phe Asp Asp Met Pro Pro Phe Ile Tyr Tyr Gly Arg
             85                  90                  95

Glu Phe Gly Ile Val Val Leu Asp Val Phe Met Phe Tyr Pro Val Leu
             100                 105                 110

Val Leu Phe Phe Leu Ser Val
             115
```

(2) INFORMATION FOR SEQ ID NO: 4:

(i) SEQUENCE CHARACTERISTICS:
       (A) LENGTH: 110 amino acids
       (B) TYPE: amino acid
       (D) TOPOLOGY: unknown (ii) MOLECULE TYPE: peptide (xi) SEQUENCE DESCRIPTION: SEQ ID NO: 4:

```
Phe Thr Asp Phe Thr Leu Cys Met Leu Thr Asp Arg Gly Val Ile Ala
 1               5                  10                  15

Asn Leu Leu Arg Tyr Asp Glu His Thr Ala Leu Tyr Asn Cys Ser Ala
             20                  25                  30

Ser Lys Thr Cys Trp Tyr Cys Thr Phe Leu Asp Glu Gln Ile Ile Thr
         35                  40                  45

Phe Gly Thr Asp Cys Asp Asp Thr Tyr Ala Val Pro Val Ala Glu Val
     50                  55                  60

Leu Glu Gln Ala His Gly Pro Tyr Ser Ala Leu Phe Asp Asp Met Pro
 65              70                  75                       80

Pro Phe Ile Tyr Tyr Gly Arg Glu Phe Gly Ile Val Val Leu Asp Val
             85                  90                  95

Phe Met Phe Tyr Pro Val Leu Val Leu Phe Phe Leu Ser Val
             100                 105                 110
```

(2) INFORMATION FOR SEQ ID NO: 5:

(i) SEQUENCE CHARACTERISTICS:
       (A) LENGTH: 23 amino acids
       (B) TYPE: amino acid
       (D) TOPOLOGY: unknown (ii) MOLECULE TYPE: peptide (xi) SEQUENCE DESCRIPTION: SEQ ID NO: 5:

```
Thr Phe Gly Thr Asp Cys Asp Asp Thr Tyr Ala Val Pro Val Ala Glu
 1               5                  10                  15

Val Leu Glu Gln Ala His Gly
             20
```

(2) INFORMATION FOR SEQ ID NO: 6:

(i) SEQUENCE CHARACTERISTICS:

(A) LENGTH: 44 amino acids
(B) TYPE: amino acid
(D) TOPOLOGY: unknown (ii) MOLECULE TYPE: peptide (xi) SEQUENCE DESCRIPTION: SEQ ID NO: 6:

```
Tyr Asn Cys Ser Ala Ser Lys Thr Cys Trp Tyr Cys Thr Phe Leu Asp
 1            5                  10                  15
Glu Gln Ile Ile Thr Phe Gly Thr Asp Cys Asp Asp Thr Tyr Ala Val
            20                  25                  30
Pro Val Ala Glu Val Leu Glu Gln Ala His Gly Pro
        35                  40
```

(2) INFORMATION FOR SEQ ID NO: 7:

(i) SEQUENCE CHARACTERISTICS:
    (A) LENGTH: 13 amino acids
    (B) TYPE: amino acid
    (D) TOPOLOGY: unknown (ii) MOLECULE TYPE: peptide (xi) SEQUENCE DESCRIPTION: SEQ ID NO: 7:

```
Ala Val Pro Val Ala Glu Val Leu Glu Gln Ala His Gly
 1            5                  10
```